(12) United States Patent
Engel et al.

(10) Patent No.: US 8,129,150 B2
(45) Date of Patent: Mar. 6, 2012

(54) MIXTURE OF REVERSIBLY INHIBITED ENZYMES

(75) Inventors: Holger Engel, Hilden (DE); Dirk Löffert, Düsseldorf (DE); Andreas Missel, Düsseldorf (DE); Ralf Peist, Hilden (DE)

(73) Assignee: QIAGEN GmbH, Hilden (DE)

( * ) Notice: Subject to any disclaimer, the term of this patent is extended or adjusted under 35 U.S.C. 154(b) by 314 days.

(21) Appl. No.: 12/295,213

(22) PCT Filed: Mar. 30, 2007

(86) PCT No.: PCT/EP2007/002866
§ 371 (c)(1),
(2), (4) Date: Sep. 29, 2008

(87) PCT Pub. No.: WO2007/115702
PCT Pub. Date: Oct. 18, 2007

(65) Prior Publication Data
US 2009/0117622 A1    May 7, 2009

(30) Foreign Application Priority Data
Apr. 4, 2006    (DE) .................. 10 2006 015 960

(51) Int. Cl.
*C12P 19/34* (2006.01)
*C12Q 1/68* (2006.01)
(52) U.S. Cl. ..................................... 435/91.2; 435/6.12
(58) Field of Classification Search .................. None
See application file for complete search history.

(56) References Cited

U.S. PATENT DOCUMENTS

| | | | |
|---|---|---|---|
| 5,338,671 A | 8/1994 | Scalice et al. ................. | 435/91.2 |
| 5,338,871 A | 8/1994 | Ngooi et al. .................. | 549/492 |
| 5,587,287 A | 12/1996 | Scalice et al. ..................... | 435/6 |
| 5,677,152 A | 10/1997 | Birch et al. .................. | 435/91.2 |
| 5,693,502 A | 12/1997 | Gold et al. .................. | 435/91.2 |
| 5,773,258 A | 6/1998 | Birch et al. .................. | 435/91.2 |
| 6,020,130 A | 2/2000 | Gold et al. ......................... | 435/6 |
| 6,183,998 B1 | 2/2001 | Ivanov et al. ................ | 435/91.2 |
| 6,667,165 B2 * | 12/2003 | Peters .......................... | 435/91.2 |

FOREIGN PATENT DOCUMENTS

| EP | 0592035 A2 | 4/1994 |
|---|---|---|
| EP | 1091002 A2 | 4/2001 |

OTHER PUBLICATIONS

Titanium™ Taq DNA polymerase published in Jan. 2001 issue of CLONTECHniques.*
Lassus et al., "Genetic alterations and protein expression of *KIT* and *PDGFRA* in serous ovarian carcinoma," *British Journal of Cancer* 91(12):2048-2055, 2004.
Kiuru et al., "Few *FH* Mutations in Sporadic Counterparts of Tumor Types Observed in Hereditary Leiomyomatosis and Renal Cell Cancer Families," *Cancer Research* 62:4554-4557, Aug. 15, 2002.
Malinen et al., "Comparison of real-time PCR with SYBR Green I or 5'-nuclease assays and dot-blot hybridization with rDNA-targeted oligonucleotide probes in quantification of selected faecal bacteria," *Microbiology* 149:269-277, 2003.

* cited by examiner

*Primary Examiner* — Teresa E Strzelecka
*Assistant Examiner* — Suchira Pande
(74) *Attorney, Agent, or Firm* — SEED IP Law Group PLLC

(57) ABSTRACT

The invention relates to composition or a kit containing an enzyme that is reversibly inhibited by means of a chemical modification and an enzyme which is reversibly inhibited using non-covalent binding, the use of a mixture of enzymes reversibly inhibited in such a manner for processing or multiplying polynucleotides, and a method for specifically amplifying DNA by simultaneously using both types of reversibly inhibited enzymes.

20 Claims, 9 Drawing Sheets

Non-covalently modified enzyme

Covalently modified enzyme

Figure 1A:
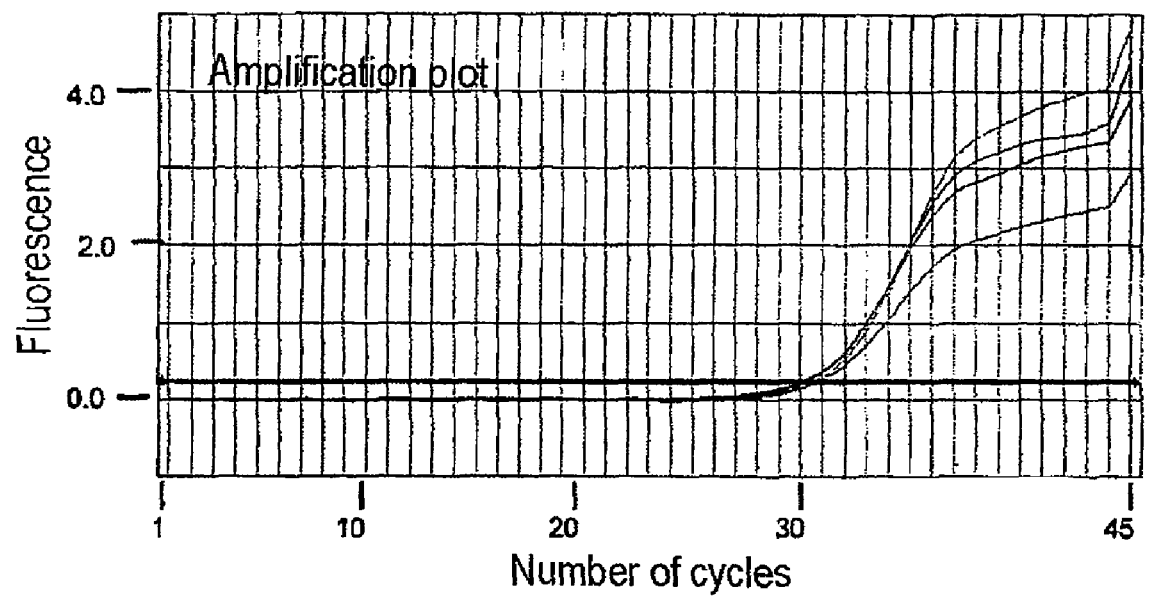
Figure 1A:
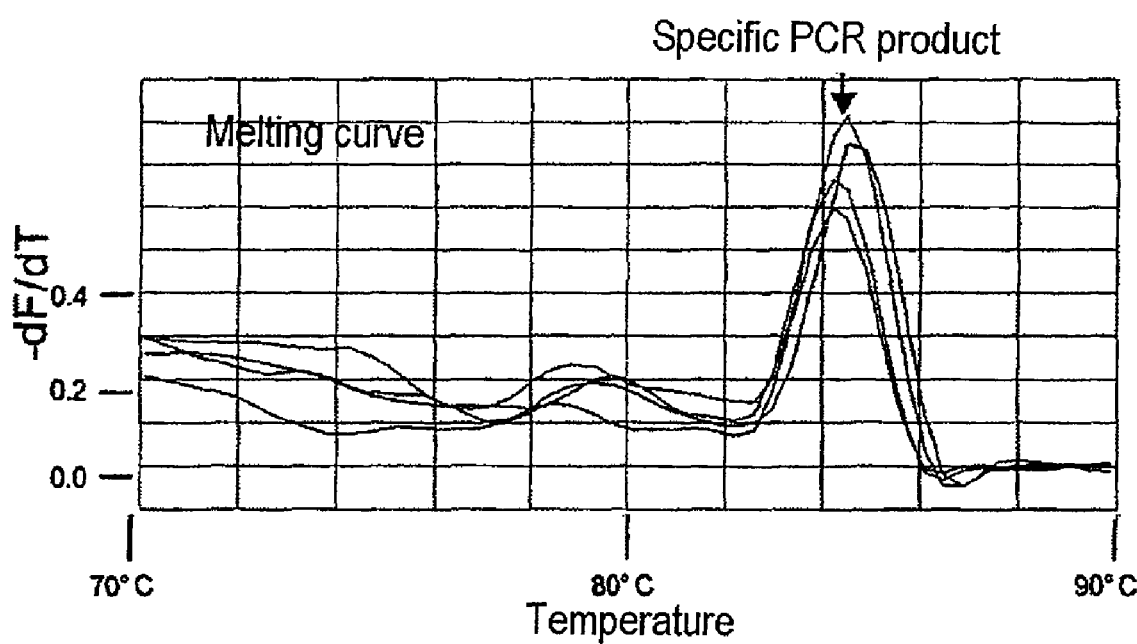

Mixture of covalently and noncovalently modified enzyme

Non-covalently modified enzyme

Covalently modified enzyme

Mixture of covalently and noncovalently modified enzyme

Non-covalently modified enzyme

Covalently modified Enzyme

Amplification plot

Melting curve

Mixture of covalently and noncovalently modified enzyme

Amplification plot

Melting curve

Specific PCR product

SEQUENCE LISTING

```
<160> NUMBER OF SEQ ID NOS: 6

<210> SEQ ID NO 1
<211> LENGTH: 21
<212> TYPE: DNA
<213> ORGANISM: artificial sequence
<220> FEATURE:
<223> OTHER INFORMATION: Primer

<400> SEQUENCE: 1
agctgaaagt tgtggaagat g                                           21

<210> SEQ ID NO 2
<211> LENGTH: 19
<212> TYPE: DNA
<213> ORGANISM: artificial sequence
<220> FEATURE:
<223> OTHER INFORMATION: Primer

<400> SEQUENCE: 2
ggagctgtct acgcaagtc                                              19

<210> SEQ ID NO 3
<211> LENGTH: 17
<212> TYPE: DNA
<213> ORGANISM: artificial sequence
<220> FEATURE:
<223> OTHER INFORMATION: Primer

<400> SEQUENCE: 3
tgctccatga ggagaca                                                17

<210> SEQ ID NO 4
<211> LENGTH: 21
<212> TYPE: DNA
<213> ORGANISM: artificial sequence
<220> FEATURE:
<223> OTHER INFORMATION: Primer

<400> SEQUENCE: 4
gtgatccaga ctctgacctt t                                           21

<210> SEQ ID NO 5
<211> LENGTH: 22
```

-continued

```
<212> TYPE: DNA
<213> ORGANISM: artificial sequence
<220> FEATURE:
<223> OTHER INFORMATION: Primer

<400> SEQUENCE: 5
aagagaagct gaagaaaacc aa                                              22

<210> SEQ ID NO 6
<211> LENGTH: 18
<212> TYPE: DNA
<213> ORGANISM: artificial sequence
<220> FEATURE:
<223> OTHER INFORMATION: Primer

<400> SEQUENCE: 6
gtggagaggt gggtgtag                                                   18
```

MIXTURE OF REVERSIBLY INHIBITED ENZYMES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770046_401USPC_SEQUENCE_LISTING.txt. The text file is 20 KB, was created on Sept. 29, 2008, and is being submitted electronically via EFS-Web.

The present invention relates to a composition or a kit that contains both an enzyme reversibly inhibited by chemical modification, and an enzyme reversibly inhibited by noncovalent binding, the use of a mixture of enzymes reversibly inhibited in this manner for the processing or amplification of polynucleotides and a method for the specific amplification of DNA and/or RNA with simultaneous use of both types of reversibly inhibited enzymes.

In the processing of polynucleotides, e.g. the multiplying, cutting, separating or ligating of polynucleotide sequences in in-vitro preparations, the polymer strands that are to be processed, preferably DNA or RNA sequences, with various required components such as suitable buffers, nucleic acid monomers, nucleic acid oligomers (e.g. PCR primers) and the enzymes and optionally coenzymes necessary or suitable for the processing desired in the particular case, are put together usually at room temperature. Then the mixture is heated to the temperature at which the enzyme or enzymes used has/have its/their optimum temperature, or specific temperature cycles are carried out. In fact, most enzymes have an optimum temperature with respect to their activity, but they are also catalytically active at other temperatures, e.g. at room temperature, to a certain extent.

By means of the polymerase chain reaction (PCR), particular DNA sequences—even from a mixture of different sequences—can be replicated considerably by using sequence-specific oligonucleotides, called "primers". This replication, generally called "amplification", takes place with the aid of a DNA polymerase. DNA polymerases form double-stranded DNA from single-stranded DNA, by attaching the bases that are in each case complementary to the single strand that remains, to free 3'-OH ends of a DNA fragment that has already been added onto the single strand. As DNA polymerases are not sequence-specific, a "filling-in" of a single-stranded region on a DNA sequence always takes place when there is partial formation of a double strand, e.g. through attachment of a DNA fragment to the single strand. During PCR, sequence-specific primers that are complementary to the sequence that is to be replicated are added to the DNA from which a particular sequence is to be amplified. However, despite the sequence-specificity, there may be nonspecific binding of these primers to single-stranded DNA, either in a region of the DNA that is not of interest, or through formation of primer dimers, i.e. through attachment of one primer to another. If this nonspecific binding occurs, the DNA polymerase fills-in the single strand that remains, so that undesirable sequences are amplified in addition to the desired DNA sequences.

Two cases frequently occur in many PCR applications: on the one hand, only very little starting material is available, and on the other hand the starting material includes a large number of very varied sequences. In the first case, owing to the initial excess of primer, primer dimer formation often occurs, with amplification of the resultant "primer double strands" instead of the desired product, whereas in the second case a nonspecific attachment of primers to other than the target sequence or sequences can lead to amplification of "incorrect" DNA sequences. In both cases this leads to reduced sensitivity of detection and even to non-detection of sequences that are present, e.g. of pathogens such as viruses and bacteria.

In view of the hoped-for "findings" from these PCR assays and the associated required sensitivity, especially in diagnostic uses of PCR it is important for the formation of such by-products to be minimized as far as possible. To achieve this aim, various methods were developed, which are nowadays generally known as "hot start PCR". In one of these methods, originally all reagents were heated to at least 72° C. before adding the DNA polymerase (Chou et al. (1992), Nucleic Acid Res. 20:1717-1723). Although this procedure did indeed increase the specificity considerably, it was impractical for more extensive assays, and in a further development of this method DNA polymerases were modified so that they were inactive at room temperature, but were activated on heating the PCR assays to the melting temperature of double-stranded DNA. Thus, these enzymes do not become active until the risk of nonspecific binding of single-stranded DNA primers due to the applied temperature is considerably less than at room temperature.

Examples of these DNA polymerases that are inactive at room temperature but can be reactivated are described in the literature, and two types are possible.

One type comprises enzymes that lose their catalytic activity as a result of a chemical modification, namely covalent binding of a chemical substance to the enzyme, until they are reactivated by heating.

U.S. Pat. Nos. 5,677,152 and 5,773,258 of Birch et al. from the years 1997 and 1998 describe e.g. inhibition of thermostable DNA polymerases by reversible chemical modification of lysine residues of the enzymes with citraconic anhydride.

U.S. Pat. No. 6,183,998 of Ivanov et al. from the year 2001 discloses a reversible chemical modification of thermostable DNA polymerases by linkage with an aldehyde, preferably formaldehyde.

The chemical modification of the enzymes often cannot be cancelled completely by a single brief raising of the temperature to 95° C., as complete renaturation in a single step could already lead to thermal degradation of the template material. In addition, the manufacturers' recommendations regarding the time for the initial activation step are as a rule less than the period of time that is required for complete reactivation. Rather, an increasing amount of the chemically modified enzymes only becomes activated in the course of the repetitive temperature cycles of a PCR. Thus, a case may arise where, at the start of PCR, there is insufficient DNA polymerase activity in the mixture, for example for completely filling-in longer templates, before the next PCR cycle begins. This can lead to incomplete synthesis of the double strand and chain terminations during PCR, with the result that, in the worst case, only fragments of the desired DNA sequence are amplified.

The second known type of reversible inhibition of DNA polymerases comprises noncovalent binding of an inhibitor to the enzyme. In this case too, the inhibition of the enzyme can be reversed by heating (e.g. at the start of PCR).

In U.S. Pat. Nos. 5,338,671 (1994) and 5,587,287 (1996), Scalice et al. describe an assay that utilizes the binding of specific antibodies to DNA polymerases in order to inhibit the activity of the particular polymerase at room temperature. By heating the PCR samples at the start of PCR, the antibody is denatured and the thermostable polymerase becomes active.

Gold et al. describe, in U.S. Pat. No. 5,693,502 (1997) and U.S. Pat. No. 6,020,130, single-stranded oligonucleotide ligands, so-called aptamers, which have high affinity for thermostable Taq and Tth polymerases at room temperature, but at elevated temperatures are no longer bound to the enzymes.

U.S. Pat. No. 6,667,165 of Peters (2003) describes the temperature-dependent and hence reversible inhibition of a thermostable DNA polymerase by complexing with polyanions. The polyanions used are not of the nucleic acid type, but comprise a monomer or an oligomer of multiple negatively charged compounds, the negative charges being due to phosphate, sulfate or carboxyl groups.

The enzymes inhibited by noncovalent binding are inactivated at room temperature, but are already almost fully activated by the initial heating step in PCR.

A disadvantage of immediate, complete activation of the enzymes inhibited by noncovalent binding is in particular that when there is a small amount of starting material to be amplified and therefore a large excess of primers, or in the case of primers whose sequences are complementary to one another to a certain extent (and therefore also "fit each other") the problems described above of nonspecific amplification or dimer formation are merely shifted by one PCR cycle, because even at the elevated temperatures during PCR there is again and again, to a certain extent, attachment of the primers to one another or to sequence regions to which the primers are not completely complementary. If at the same time there is high polymerase activity in the mixture, the "mismatches" are tolerated and the polymerase becomes active before the sequence that does not match completely can be detached again. As a result there is amplification of unwanted sequences.

The aim of the present invention was to offer the possibility of improving the results in the processing or amplification of polynucleotides, in particular longer polynucleotide sequences, without having to suffer a deterioration of amplification specificity.

This aim is achieved with a composition that contains both an enzyme reversibly inhibited by chemical modification, and an enzyme reversibly inhibited by noncovalent binding, or a mixture thereof, with a kit that contains both said enzymes or a mixture thereof, as well as with a use of a mixture of said enzymes and a method with simultaneous use of said enzymes.

The simultaneous use, or the simultaneous inclusion of the two enzymes reversibly inhibited in different ways together in the same charge, e.g. for the processing or amplification of polynucleotides, or the provision of both enzymes in a kit for combined use in an assay is an object of the present invention.

The advantage of the simultaneous use of an enzyme that has been reversibly inhibited by a chemical modification and an enzyme that has been reversibly inhibited by noncovalent binding, is that the noncovalent binding can be reversed quickly and therefore an amount of active enzyme that can be specified in advance is quickly prepared, whereas the chemical modification of the enzyme cannot be reversed so quickly, but to an increasing extent over time, so that in the course of a reaction more and more activity of an enzyme can be made available, without the need for additional processing steps or manipulations.

In principle, the assay forming the basis of this invention can be used in any application in which a certain predetermined amount of enzymatic activity is required at a specified point of time, but the required amount of enzymatic activity increases in the course of time, e.g. for the duration of a reaction that is taking place. An example of this is amplification by PCR, as described in more detail below, though without being limited to this. The assay according to the present invention can also be chosen in the case when it is advantageous if an enzyme is active with a time shift relative to another enzyme. An example of this is reverse transcription and subsequent PCR of the cDNA obtained, or the cutting and subsequent ligation of DNA. The advantage of having both enzymes present together in an assay is that fewer processing steps are necessary and hence operation can be much more efficient, especially when very many samples have to be processed simultaneously, but also, for example, the risk of contamination of the samples can be reduced considerably.

According to the invention, the inhibition of the enzymes used is reversible. The manner of cancelling or reversing the inhibition depends on the type of modification of the enzymes. The manner of cancelling or reversing the inhibition should be selected so that the activity of the enzyme can be recovered. That is to say, not only the modification or complexing by noncovalent binding of the enzyme is cancelled, but also on cancelling the modification/complexing an enzyme is obtained again that is able to catalyze the reaction that it was able to catalyze before the modification/complexing. In a preferred embodiment of the invention, the modification (covalent binding) or the complexing (non-covalent binding) of the enzyme can be cancelled by supply of heat. In this case it is advantageous if the enzyme is thermally stable. Another possibility for cancellation is by changing the pH value in the mixture. In this case the enzyme should tolerate change in pH, or the pH should be changed to the region in which the enzyme displays its optimum activity.

In a preferred embodiment of the invention, the enzymes under consideration here are those that are able to "process" or to multiply polynucleotides. The term "polynucleotide" means a sequence of nucleotides containing more than one base, preferably a sequence of at least 8 nucleotides. The sequence can be single-stranded or double-stranded, or (also partially) in the form of a triple helix. It can comprise DNA, RNA or DNA-RNA hybrids.

Enzymes that can preferably be used according to the present invention are DNA polymerases, RNA polymerases, ligases, reverse transcriptases and restriction endo- or exonucleases. These enzymes can be combined depending on the desired "processing" of the polynucleotides. In an especially preferred embodiment it is also possible to use two enzymes with the same catalytic capacity (i.e. the enzymes catalyze the same reaction), where according to the invention one enzyme contains a reversible chemical modification via covalent binding of an inhibitor and the other enzyme contains a reversible noncovalent binding of an inhibitor. It is quite especially preferred if the two enzymes used are polymerases, in particular thermostable polymerases, especially preferably thermostable DNA polymerases, that are used according to the invention in order to generate and amplify specific DNA sequences in a PCR.

The term "thermostable" means that the corresponding enzyme does not (completely) lose its activity even when heated to 98° C. and generally has optimum activity in the range between 40° C. and 90° C., preferably in the range between 50° C. and 80° C. Said thermostable enzymes are generally known in technical circles and are also marketed under the definition "thermostable".

The term "polymerase" means a DNA polymerase or an RNA polymerase, in particular a DNA polymerase or a reverse transcriptase.

DNA polymerases that can be inhibited reversibly by chemical modification or by noncovalent binding of an inhibitor are e.g. thermostable DNA polymerases from the species *Thermus, Pyrococcus, Thermococcus, Thermotoga,*

*Pyrodictium* and *Thermosipho*, preferably *Thermus aquaticus*, *Thermus thermophilus*, *Thermus flavus*, *Thermus filiformis*, *Pyrococcus furiosus*, *Pyrococcus woesei*, *Pyrococcus* spec. (strain KOD1), *Pyrococcus* spec. GB-D, *Thermococcus litoralis*, *Thermococcus* sp.9° N-7, *Thermotoga maritima*, *Pyrococcus* spec. ES4 (*endeavori*), *Pyrococcus* spec. OT3 (*horikoshii*), *Pyrococcus profundus*, *Thermococcus stetteri*, *Thermococcus* spec. AN1 (*zilligii*), *Thermococcus peptonophilus*, *Thermococcus celer*, *Thermococcus fumicolans*, *Pyrodictium occultum*, *Pyrodictium abyssi* or *Thermosipho africanus*.

Examples of suitable reverse transcriptases are MMLV reverse transcriptase, AMV reverse transcriptase, RSV, HIV-1 reverse transcriptase and HIV-2 reverse transcriptase, without being limited to these.

In a preferred embodiment, the enzyme that, according to the invention, has been reversibly inhibited by a chemical modification is at least one of these thermostable polymerases, which has been reversibly inhibited by reversible linkage of at least one of its lysine residues with a citraconic anhydride, and the inhibition can be reversed by the supply of heat (for details of this reversible linkage see U.S. Pat. Nos. 5,773,258 and 5,677,152), or by reversible linkage or crosslinking of the amino acid side chains with an aldehyde, preferably a formaldehyde, and once again the resultant inhibition can be reversed by the supply of heat (for details of this linkage see U.S. Pat. No. 6,182,998). The enzyme that has been reversibly inhibited by noncovalent binding of an inhibitor, is, according to the preferred embodiment of the invention, also at least one of the aforementioned polymerases, which at room temperature, however, are either inhibited by a nucleotide aptamer, the nucleotide aptamers described for example in U.S. Pat. No. 5,693,502 being especially suitable, is inhibited by attachment of an antibody, as described for example in U.S. Pat. Nos. 5,587,287 and 5,338,871, or is complexed by a polyanion, as described e.g. in U.S. Pat. No. 6,667,165.

Preferably the enzymes according to the present invention are used in a unit ratio of chemically modified enzyme to enzyme modified by noncovalent binding from 0.1:1 to 100:1.

The definition of unit of the various enzymes mentioned here is as follows:

DNA polymerases: one unit is defined as the amount of enzyme which, under optimized reaction conditions (temperature, buffer composition), in 30 minutes, incorporates 10 nmol DNTP in acid-insoluble material using activated DNA as template.

Reverse transcriptases: one unit is defined as the amount of enzyme which, under optimized reaction conditions (temperature, buffer composition), in 10 minutes, incorporates 1 nmol dNTP in acid-insoluble material using poly(rA)●p(dT) 12-18 as template/primer.

DNA ligases: a Weiss unit is defined as the amount of enzyme which, under optimized reaction conditions (temperature, buffer composition), in 20 minutes, catalyzes the conversion of one nanomol [32PPi] to a Norit-adsorbable form.

RNA ligases: one unit is defined as the amount of enzyme which, under optimized reaction conditions (temperature, buffer composition), in 30 minutes, catalyzes the conversion of 1 nmol of 5'-phosphoryl ends in 5'-[32P]-poly(A)12-18 to a phosphatase-resistant form.

Restriction endonucleases: one unit is defined as the amount of enzyme which, under optimized reaction conditions (temperature, buffer composition), in one hour, catalyzes the complete digestion of 1 μg of substrate DNA.

Exonucleases: one unit is defined as the amount of enzyme which, under optimized reaction conditions (temperature, buffer composition), in 30 minutes, catalyzes the release of 1 nmol of acid-soluble nucleotides.

In a preferred embodiment of the invention, the two enzymes are used for processing and/or amplifying RNA or DNA samples by known methods of genetic engineering. Said methods are for example reverse transcription of RNA to cDNA, combined reverse transcription and PCR amplification in one reaction ("one-step RT-PCR"), DNA amplification by a polymerase chain reaction (PCR), cutting of DNA using restriction enzymes, ligation of DNA and similar methods, without being limited to these. An especially preferred "processing technique" is PCR, optionally preceded by reverse transcription, which leads to replication (amplification) of specific DNA sequences.

The procedure in PCR, optionally preceded by reverse transcription of RNA to cDNA, is known by a person skilled in the art and only a brief outline will be given in the following, based on an example. It should be pointed out that apart from the example of PCR given below with one sequence-specific primer pair, several variants of PCR are possible, e.g. using primers that deliberately contain "mismatches", or through various combinations of suitable and less suitable primers, and all these variants are to be carried out with the assay according to the invention, described here.

In reverse transcription, first an RNA-DNA hybrid is constructed from RNA (single-stranded), preferably mRNA. The resultant DNA template (cDNA) corresponds to (is complementary to) the information "filed" on the mRNA.

By including said cDNA or a DNA sample isolated in some other way in a PCR, using sequence-specific primers it is possible to produce double-stranded DNA, and optimally only the sequences are amplified that include the sequences of the primers. In each cycle of PCR the DNA double strand is first melted (the strands are separated), then there is attachment of mutually suitable sequences, preferably of the primers to their templates, followed by filling-in of the single-stranded regions by "linking" of the "suitable" nucleotides in each case by the DNA polymerase, once again obtaining a DNA double strand. In each cycle, the DNA sequences constructed in the preceding cycle are additionally available as templates, therefore there is an exponential increase in the DNA sequence or sequences that include the primer sequences. For this reason, in a PCR more and more polymerase activity is required with increasing number of cycles, in order to ensure that the specific sequence is actually amplified.

Especially in diagnostic assays or in so-called "real-time PCR" it is important to ensure sufficient enzymatic activity at every point of time, so that there is neither premature "breakaway" from the exponential increase of the desired PCR, nor chain terminations, e.g. because the next cycle (beginning with melting of the double-stranded DNA) starts before the polymerase has been able to fill-in the single strand completely. Both lead to impairment of the sensitivity of the method.

The present invention is based on the finding that when using only polymerases that are reversibly inhibited by non-covalent binding of an inhibitor in particular with small starting amounts of templates or a small copy number of the target molecule (DNA with the desired sequence) at the start of PCR, owing to almost complete activation of the enzyme nonspecific primer hybridization events lead to amplification of nonspecific products. If the composition of the reaction buffer used does not ensure high hybridization specificity and/or the sequences of the primers promote mutual hybridization, due to the high polymerase activity from the start of the PCR there is increased risk of formation of nonspecific PCR products. The nonspecific "by-products" formed at the start of PCR also serve as template in the subsequent cycles, just like the desired sequence.

When only chemically modified enzymes are used, conversely, there is the problem described above, that possibly at the start of PCR insufficient polymerase activity is available for the DNA sequence, to which the primers have bound specifically, to be filled-in completely in each case in the course of the PCR cycle, so that in this case undesirable chain terminations can occur. The manufacturers of said systems inhibited by chemical modification therefore recommend carrying out an initial incubation of the samples for an extended period of time (typically 2 to 15 min) at temperatures above 90° C. However, even after this incubation time these enzymes have usually still not regained their full activity. Activation can only be assumed to be optimum after several incubation cycles with temperatures in this range.

Based on this finding, according to the present invention the approach was selected for the processing and amplification of DNA sequences, in particular in a PCR, of using both a "fast-activated" enzyme, as well as an enzyme "increasingly activated" over time, in order to obtain optimal results and to minimize the disadvantages described above.

Therefore, for example, both a thermostable DNA polymerase reversibly inhibited by noncovalent binding of an inhibitor, in an amount that is sufficient at the start of PCR to provide a DNA polymerase activity that ensures, after a specific hybridization of a primer to the single-stranded DNA, the complete "filling-in" to the double strand, and a thermostable DNA polymerase reversibly inhibited by chemical modification in an amount that ensures that, in the course of the PCR cycles sufficient enzymatic activity is provided so that the exponential multiplication of the DNA is also still ensured in "late" cycles, are included in a composition for the processing of DNA, e.g. a PCR charge. Thus, in accordance with this approach, in each phase of the PCR the necessary amount of active enzyme is adjusted to the amounts of template to be amplified.

Preferably, this mixture is selected when the size of the amplicon to be amplified is larger than about 200 bp, because especially with larger amplicons there is a risk of chain termination through incomplete synthesis of the complementary strand, if there is insufficient enzymatic activity in the mixture.

In a preferred embodiment the "fast-activated" polymerase, i.e. reversibly inhibited by noncovalent binding, and the "increasingly activated" DNA polymerase, i.e. reversibly inhibited by chemical modification, are used in a unit ratio from 1:0.1 to 1:100. Especially preferably, the fast-activated polymerase is used, at most, in the same proportions as the chemically modifiable polymerase, even more preferably in deficit relative to the chemically modified polymerase.

According to the invention, a composition or a kit, preferably a composition or a kit for the processing or amplification of polynucleotides, especially preferably for carrying out a PCR, contains both enzymes together.

Furthermore, the composition or the kit can, depending on the desired application, contain other required materials or reagents that are suitable or necessary for the desired application. For example, a composition or a kit for PCR can contain, in addition to the enzymes, a suitable buffer, dNTPs (dATP, dITP, dUTP, dGTP, dTTP, dCTP or derivatives thereof), optionally cofactors such as $MgCl_2$, optionally primers, optionally DNA as reference template, or other components. The components required or suitable for reverse transcription, ligation or cutting by means of restriction nucleases are completely known by a person skilled in the art and can be found in any laboratory manual or in the technical literature.

FIGURES

The top part of FIG. 1a shows the amplification plot, showing the increase in double-stranded DNA in the course of PCR by amplification with noncovalently modified enzyme. Details of the PCR can be found in Example 1a. The bottom part of FIG. 1a shows the melting curve of the resultant PCR product.

Figure 1B:
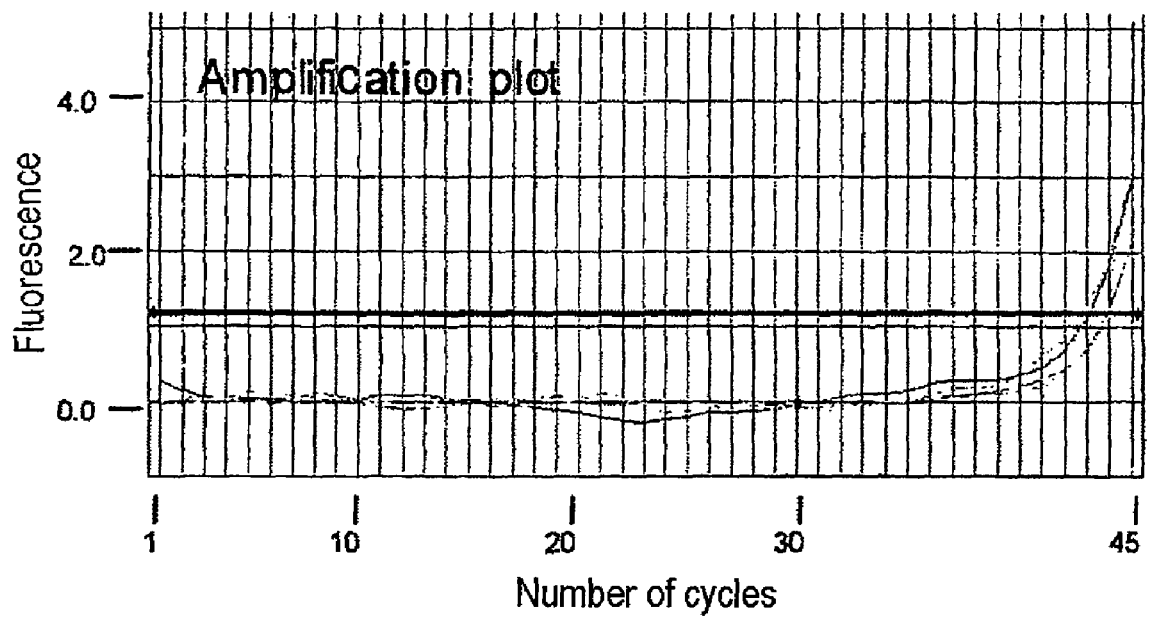
Figure 1B:
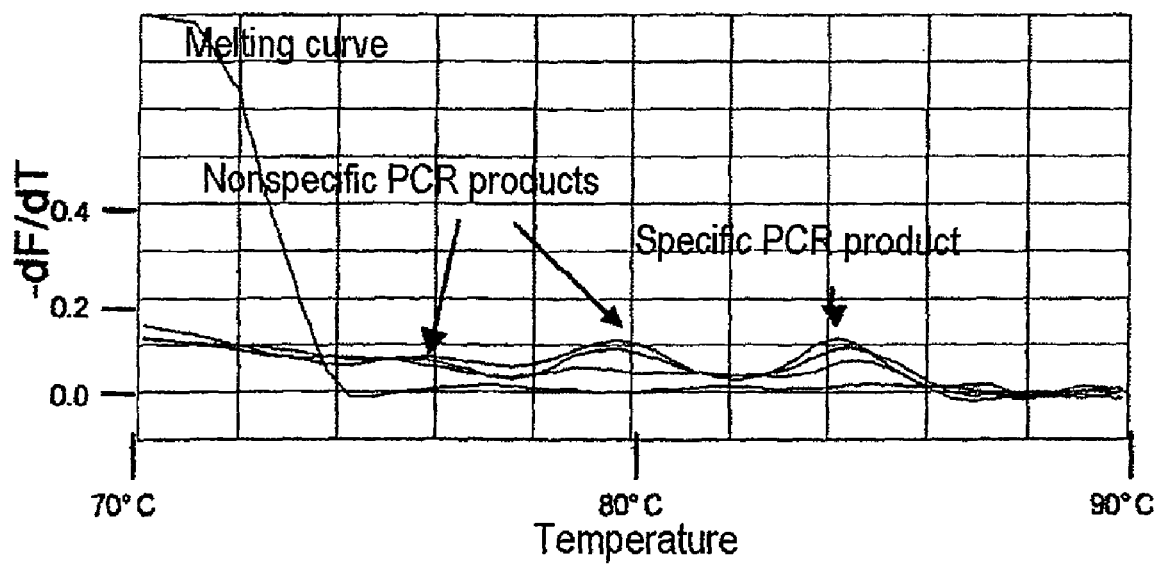

The top part of FIG. 1b shows the amplification plot, showing the increase in double-stranded DNA in the course of PCR by amplification with covalently modified enzyme. Details of the PCR can be found in Example 1b. The bottom part of FIG. 1b shows the melting curve of the resultant PCR product(s).

Figure 1C:
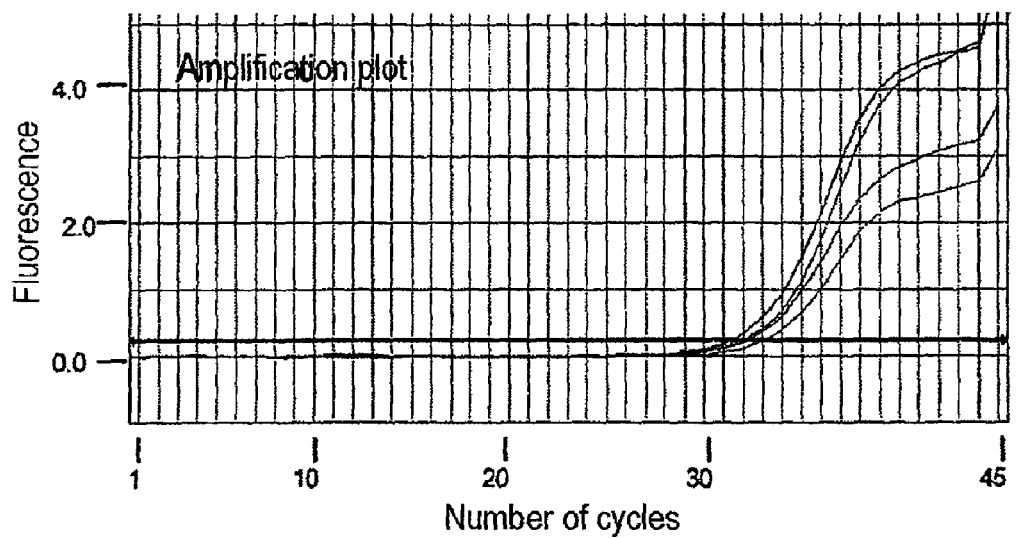
Figure 1C:
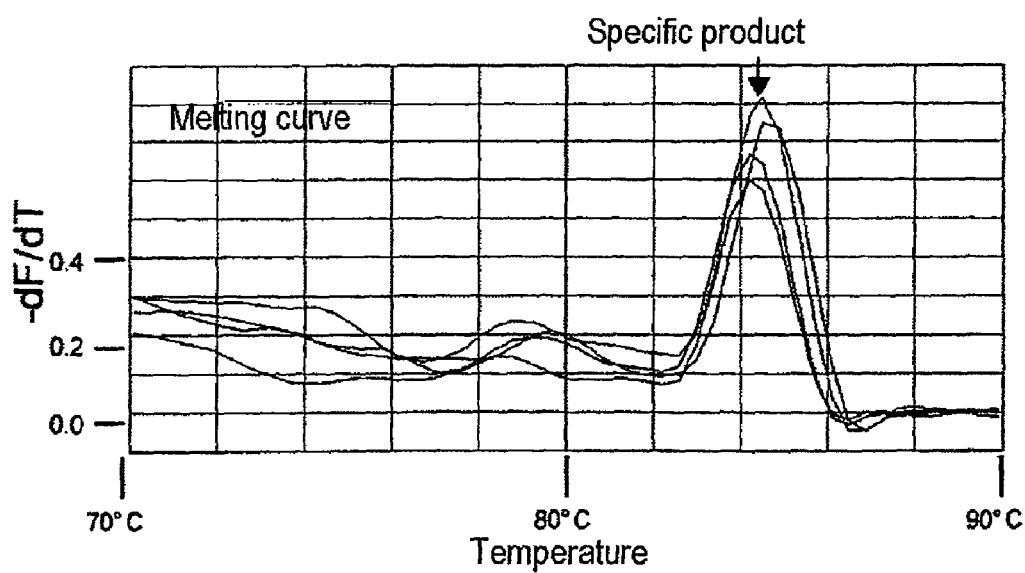

The top part of FIG. 1c shows the amplification plot, showing the increase in double-stranded DNA in the course of PCR by amplification with a mixture of noncovalently modified enzyme and covalently modified enzyme. Details of the PCR can be found in Example 1c. The bottom part of FIG. 1c shows the melting curve of the resultant PCR product.

Figure 2A:
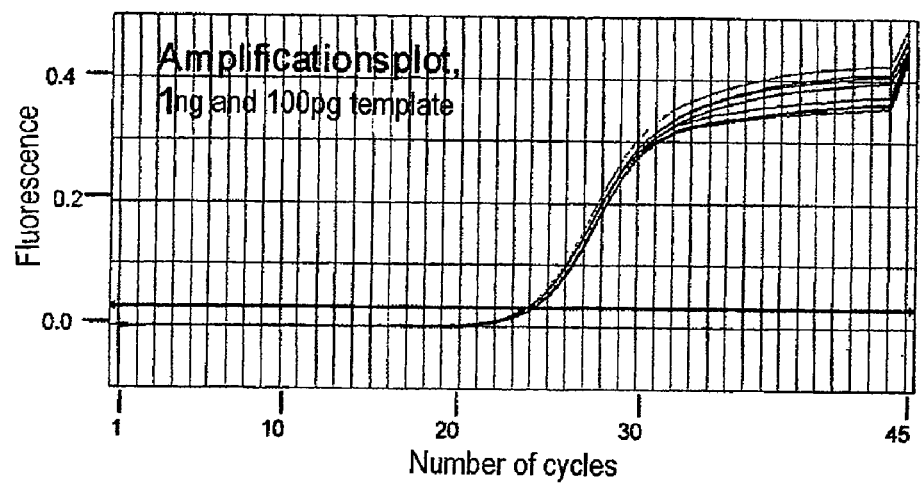
Figure 2A:
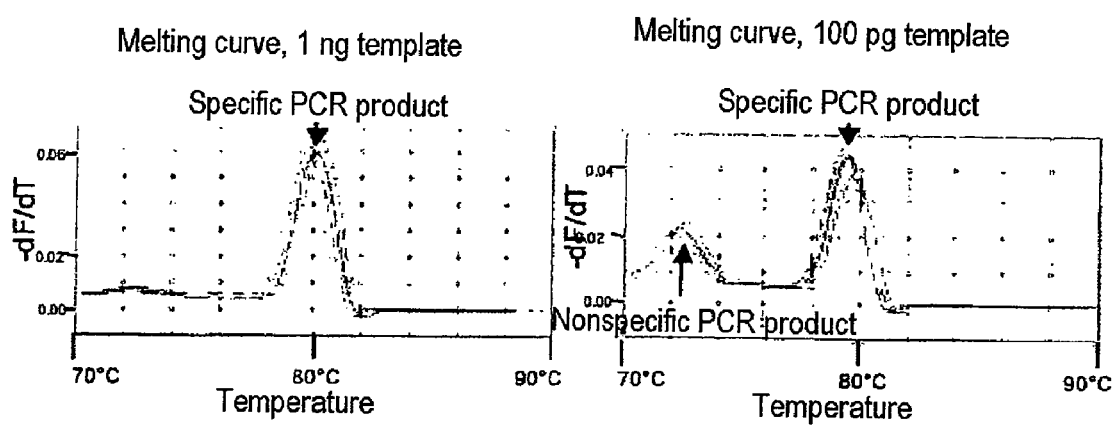

The top part of FIG. 2a shows the amplification plot, showing the increase in double-stranded DNA using different starting amounts of DNA in the course of PCR by amplification with noncovalently modified enzyme. Details of the PCR can be found in Example 2a. The bottom part of FIG. 2a shows the melting curves of the resultant PCR products.

Figure 2B:
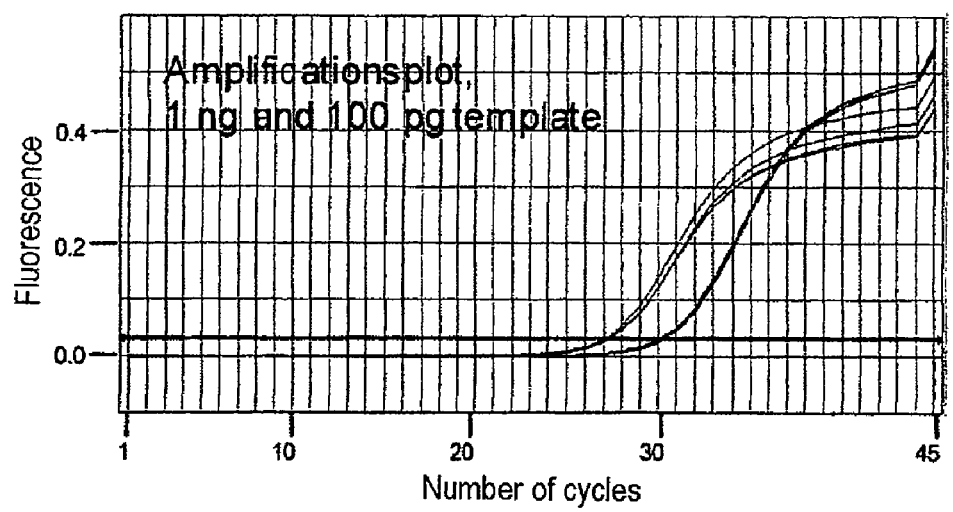
Figure 2B:
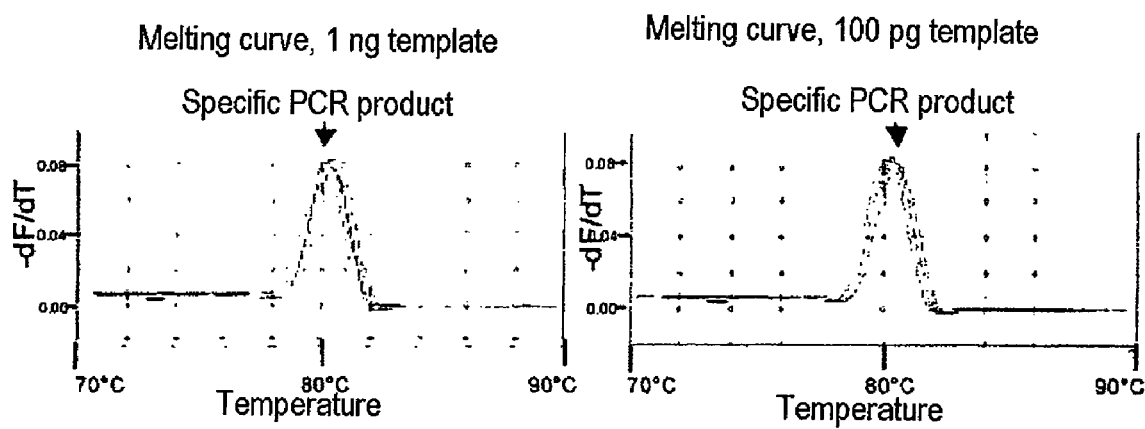

The top part of FIG. 2b shows the amplification plot, showing the increase in double-stranded DNA using different starting amounts of DNA in the course of PCR by amplification with covalently modified enzyme. Details of the PCR can be found in Example 2b. The bottom part of FIG. 2b shows the melting curves of the resultant PCR products.

Figure 2C:
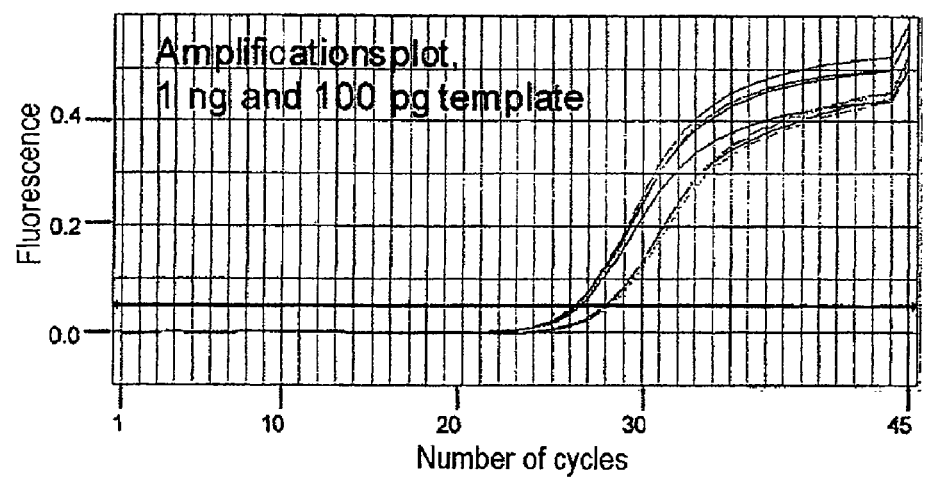
Figure 2C:
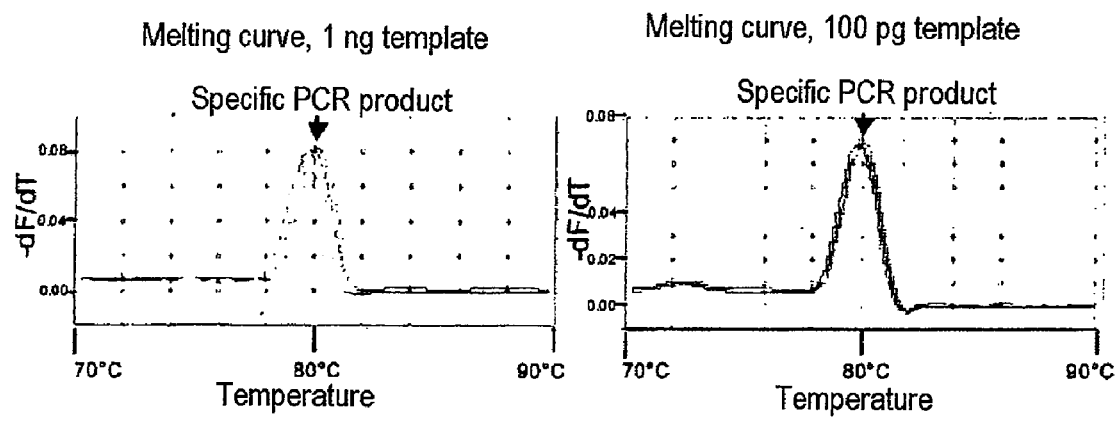

The top part of FIG. 2c shows the amplification plot, showing the increase in double-stranded DNA using different starting amounts of DNA in the course of PCR by amplification with a mixture of noncovalently modified enzyme and covalently modified enzyme. Details of the PCR can be found in Example 2c. The bottom part of FIG. 2c shows the melting curve of the resultant PCR products.

Figure 3A:
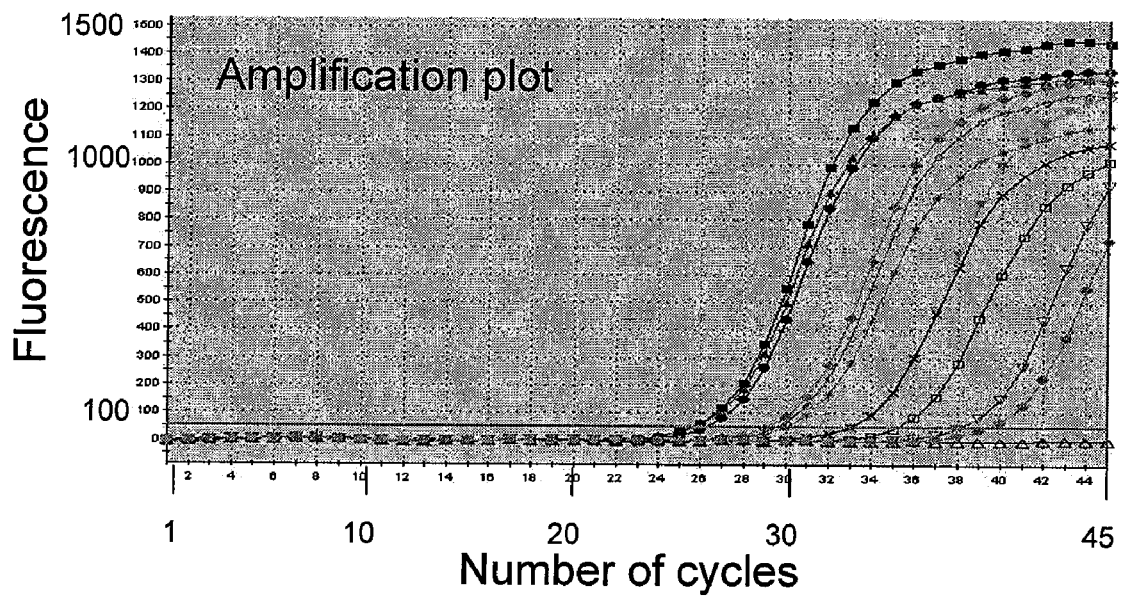
Figure 3A:
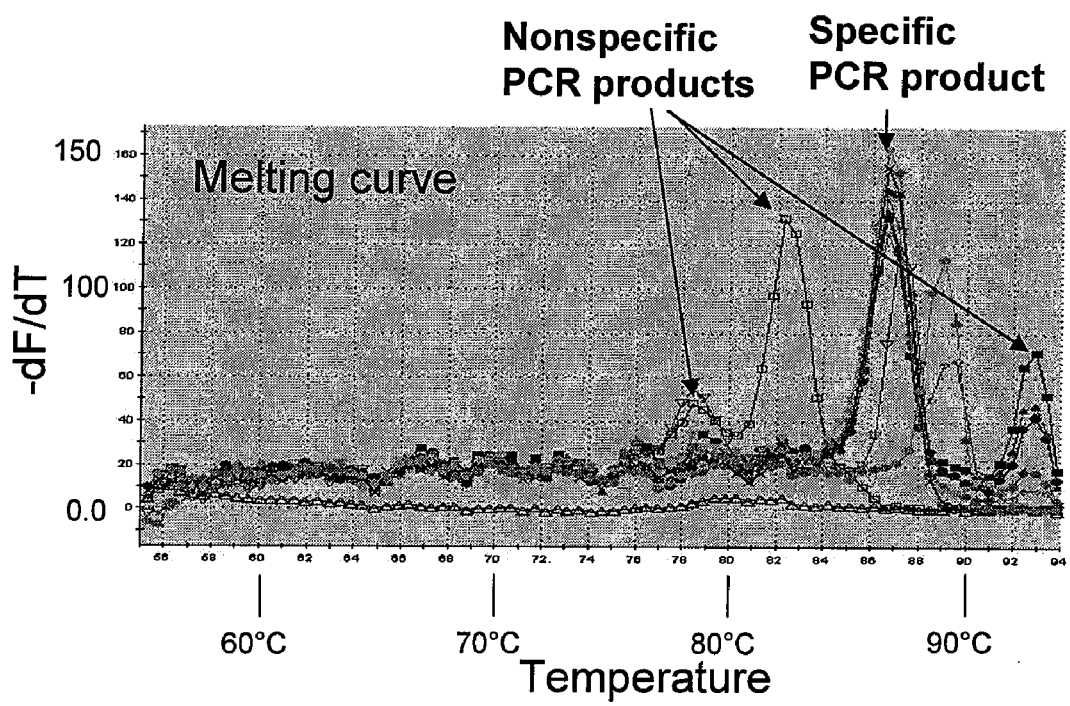

The top part of FIG. 3a shows the amplification plot, showing the increase in double-stranded DNA in the course of PCR by amplification with noncovalently modified enzyme. Details of the PCR can be found in Example 3a. The bottom part of FIG. 3a shows the melting curve of the resultant PCR products.

Figure 3B:
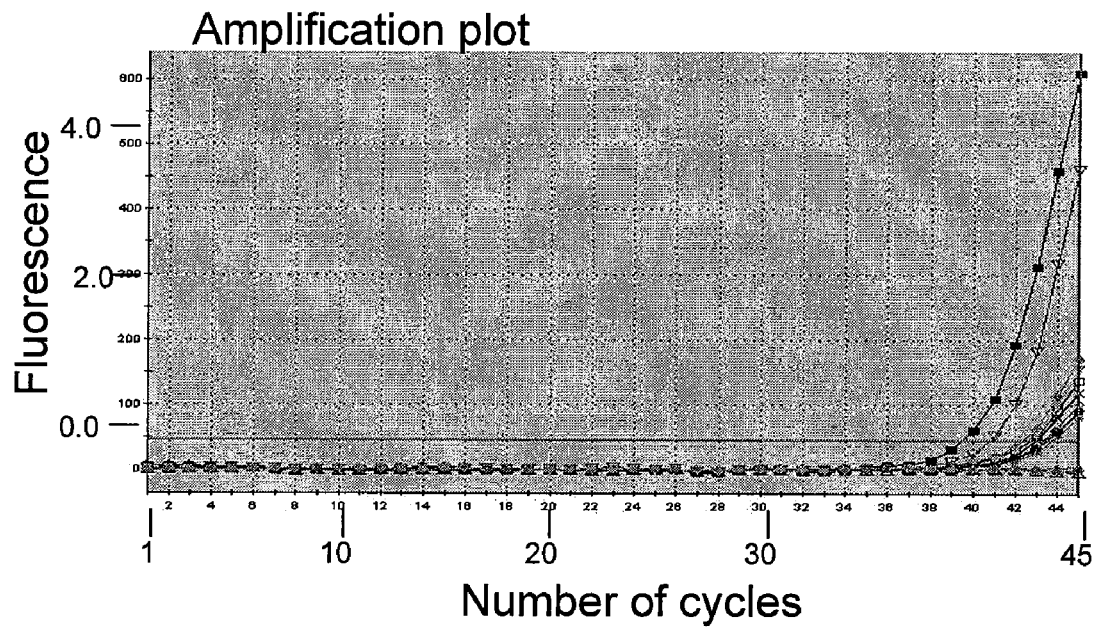
Figure 3B:
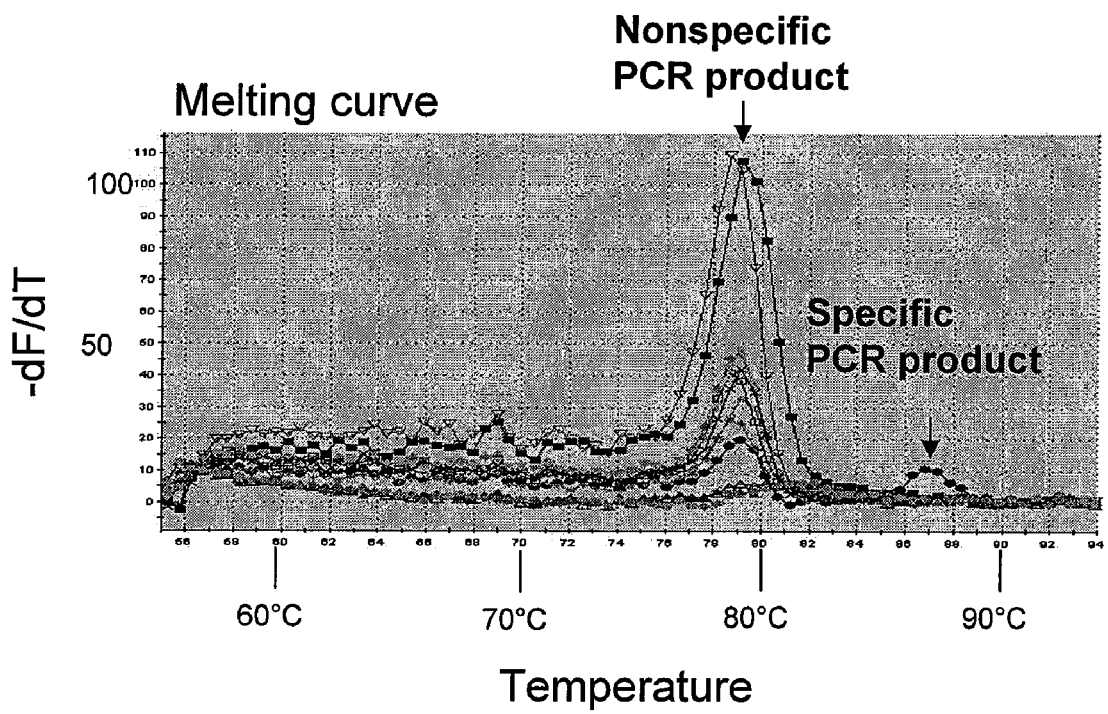

The top part of FIG. 3b shows the amplification plot, showing the increase in double-stranded DNA in the course of PCR by amplification with covalently modified enzyme. Details of the PCR can be found in Example 3b. The bottom part of FIG. 3b shows the melting curve of the resultant PCR products.

Figure 3C:
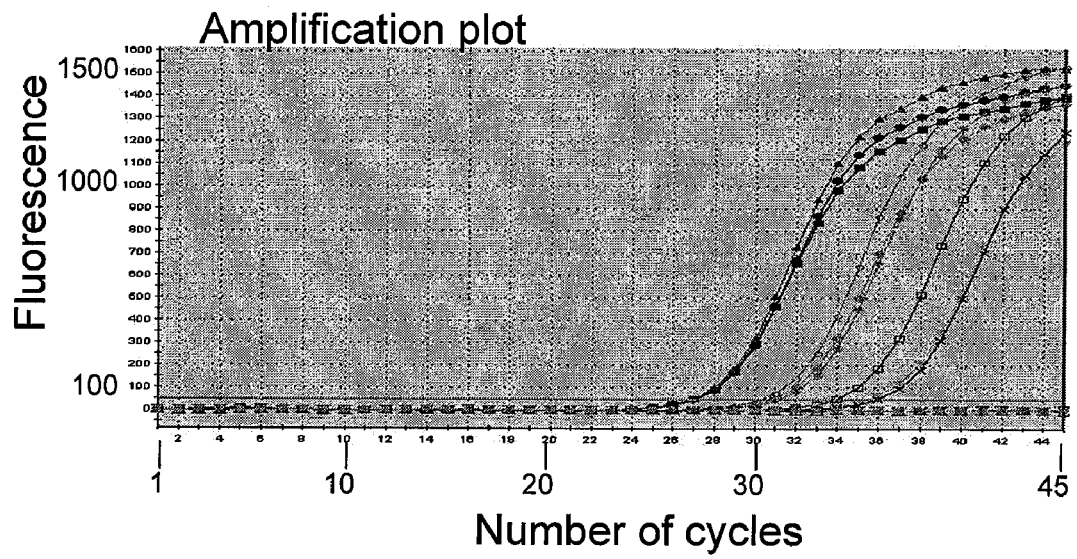
Figure 3C:
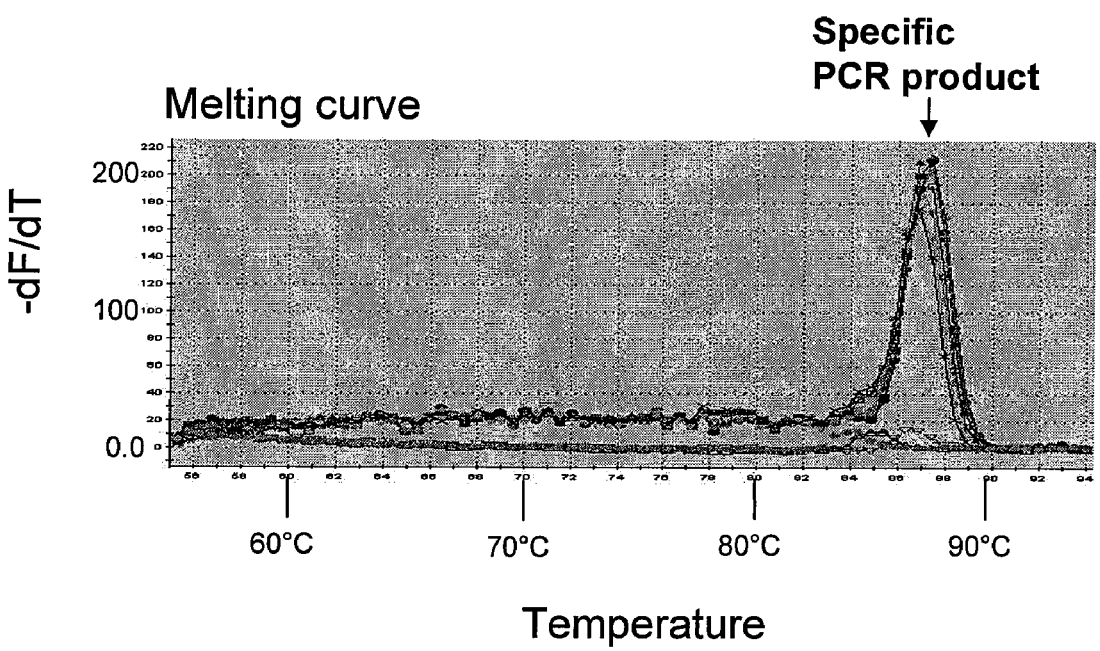

The top part of FIG. 3c shows the amplification plot, showing the increase in double-stranded DNA in the course of PCR by amplification with a mixture of noncovalently modified enzyme and covalently modified enzyme. Details of the PCR can be found in Example 3c. The bottom part of FIG. 3c shows the melting curve of the resultant PCR product.

EXAMPLES

The following examples aim to explain the invention in more detail, without limiting it to these examples of application.

Example 1

Amplification of a long PCR fragment in real-time PCR with SYBR Green based detection with covalently and noncovalently modified DNA polymerases To investigate the effect of differently modified thermostable DNA polymerases on the amplification of long DNA fragments, a 690 base pair fragment of the transcript for the human CTNNA1 gene (NM_001903) was amplified. The primers used for this had the following sequences:

```
Forward primer: AGCTGAAAGTTGTGGAAGATG  (Seq ID No:1)
Reverse primer: GGAGCTGTCTACGCAAGTC    (Seq ID No:2)
```

The amplification was carried out with a modified version of the QuantiTect SYBR Green PCR Master-Mix (QIAGEN GmbH, Hilden), which apart from primers and template contains all necessary components for SYBR Green-based real-time PCR (i.e. Tris, potassium chloride, magnesium chloride, ammonium sulfate, dNTP-nucleotides, SYBR Green). The modification comprised omission of the HotStarTaq DNA polymerase (QIAGEN), which is already contained in the commercially available product. In each case, the following enzymes were used instead:

1. HotMasterTaq DNA polymerase (Eppendorf AG, Hamburg), an enzyme which, according to U.S. Pat. No. 6,667,165, undergoes temperature-dependent inhibition by noncovalent complexing with a non-nucleic acid-type polyanion and develops its full activity at temperatures above 55° C. (called "noncovalently modified enzyme" in the following): the amount used was 1.5 units per reaction
2. Taq-DNA polymerase, which according to U.S. Pat. No. 6,183,998 was covalently modified with formaldehyde and hence inhibited (QIAGEN, Hilden) (called "covalently modified enzyme" in the following). The amount used was 1.25 units per reaction
3. A mixture of the noncovalently and the covalently modified enzyme, at a ratio of 0.125 units noncovalently modified enzyme to 1.25 units covalently modified enzyme per reaction.

The final volume of the reaction mixture was in each case 25 μl, and the primers were used at a final concentration of 0.3 μM. It was carried out on the ABI PRISM 7000 Sequence Detection System (Applied Biosystems). 1 ng cDNA, prepared from HeLa-RNA, per reaction, served as template. In each case 4 replicates were analyzed per enzyme or enzyme mixture.

The reaction conditions were as follows:
A: Initial denaturation of the template/activation of the enzyme
95° C., 5 minutes
B: Amplification:
Denaturation: 95° C., 15 seconds
Primer annealing: 55° C., 30 seconds
Primer extension: 72° C., 30 seconds
Fluorography during the extension in each cycle
Number of cycles: 45

C: Melting curve analysis
Initial denaturation of the PCR product: 95° C., 15 seconds
Rehybridization of the PCR product: 60° C., 20 seconds
Melting of the PCR product: heating from 60° C. to 95° C. at a heating rate of approx. 0.2° C./s
Fluorography during melting of the PCR product The reaction mixtures were assayed at room temperature.

As is clear from FIG. 1a, the desired 690 bp fragment was successfully amplified using the noncovalently modified enzyme, as shown by combined analysis of the amplification plot and melting curve analysis. The "threshold", i.e. the fluorescence value that is well above the background fluorescence, is reached at PCR cycle 30.5. The melting temperature of the PCR product is at the expected 84° C.; the proportion of other, nonspecific products is negligible in comparison with the specific product. Thus, an immediately-reactivated, noncovalently modified enzyme is advantageous for a long amplificate of this kind.

FIG. 1b provides evidence of failure of amplification of the same fragment when using only a covalently modified thermostable DNA polymerase. Firstly, a discernible increase in fluorescence only occurs in a very late PCR cycle (43.5), and moreover only for three out of four replicates. Secondly, melting curve analysis shows that a high proportion of the products formed are undesirable amplificates such as primer dimers and other nonspecific reaction products.

The method of detection chosen here, using the fluorescence dye SYBR Green, does not discriminate between specific and nonspecific PCR product. SYBR Green is a dye that attaches sequence-independently to double-stranded DNA and following attachment and simultaneous excitation by a light source, emits fluorescence. This means, for the example shown in FIG. 1b, that the increase in fluorescence in the amplification plot not only occurs very late, but is also still primarily due to the detection of nonspecific products. Thus, a covalently modified enzyme that cannot be completely reactivated immediately is not advantageous for a long amplificate of this kind.

FIG. 1c demonstrates the advantages of a combination of covalently and noncovalently modified enzymes. By adding a small amount of immediately-reactivated, noncovalently modified enzyme, as shown in FIG. 1b, the results are improved dramatically and are very similar to those shown under FIG. 1a both with respect to sensitivity (comparable number of cycles when the threshold is crossed) as well as specificity (high yield of specific product).

Example 2

Amplification of a PCR fragment in real-time PCR with SYBR Green based detection with covalently and noncovalently modified DNA polymerases using a primer combination with a tendency to dimer formation.

To investigate the effect of differently modified thermostable DNA polymerases on amplification using primers with a tendency to dimer formation, a 129 base pair fragment of the transcript for the human MYC gene (NM_002467) was amplified. The primers used for this had the following sequences:

```
Forward primer: TGCTCCATGAGGAGACA      (Seq ID No:3)
Reverse primer: GTGATCCAGACTCTGACCTTT  (Seq ID No:4)
```

The reactions were set up as described in Example 1. As a departure from Example 1, in one assay 1 ng, and in another assay 100 pg cDNA, prepared from HeLa-RNA, were used as template amount per reaction. This time it was carried out on the ABI PRISM 7500 Sequence Detection System (Applied Biosystems).

As is clear from FIG. 2a, using the noncovalently modified enzyme it was not possible to discriminate between the two different amounts of template. Analysis of the amplification plot shows that all samples cross the fluorescence threshold value at the same PCR cycle. It is to be expected that when using the smaller amount of template, the threshold value should be crossed much later. The reason for this follows from the separate analysis of the melting curve for the two amounts of template used. When using the larger amount of template there is exclusive formation of the specific PCR product with a melting temperature of 80° C., but with the smaller amount of template, in addition to the specific product there is still formation of nonspecific PCR products, which on the basis of their lower melting temperature can be identified as typical primer dimers. The formation of these primer dimers can be attributed to the high initial activity of the DNA polymerase immediately after the initial denaturation. With a small amount of template the proportion of unannealed primers is particularly high, therefore a comparatively large amount of active polymerase right at the start of the reaction leads to increased formation of these PCR artifacts. As these, as explained in Example 1, also contribute to generation of the fluorescence signal, discrimination between the two amounts of template, and hence the desired quantification, are no longer possible. Thus, an immediately-reactivated, noncovalently modified enzyme is not advantageous for an amplificate of this kind with primers having a tendency to dimer formation.

FIG. 2b demonstrates the successful specific amplification of the same fragment when using only a covalently modified thermostable DNA polymerase and therefore successful discrimination of the two amounts of template used. The amplification plot shows the expected, cycle-shifted crossing of the fluorescence threshold; the melting curve provides evidence of the specific amplification for the two amounts of template. Thus, a covalently modified enzyme that cannot be completely reactivated immediately is advantageous for an amplificate of this kind with primers with a tendency to dimer formation.

FIG. 2c demonstrates the advantageous combination of covalently and noncovalently modified enzymes. By adding a small amount of immediately-reactivated, noncovalently modified enzyme, as shown in FIG. 2a, the results were improved dramatically, achieving results that are very similar to those shown under FIG. 2b both with respect to sensitivity (comparable number of cycles when the threshold is crossed) and specificity (high yield of specific product).

Example 3

Amplification of a PCR fragment in real-time PCR with SYBR Green-based detection with covalently and noncovalently modified DNA polymerases, which were produced using different methods of covalent or noncovalent modification In order to demonstrate that the advantageous effect of the combination of differently modified thermostable DNA polymerases is not limited to a particular type of covalent and noncovalent modification, for the PCR presented in this example a combination of two enzymes was used, both of which differ in their type of modification from the enzymes used in Examples 1 and 2. The following two DNA polymerases were used.

1: Covalently modified enzyme:

AmpliTaq Gold (Applied Biosystems. Foster City, Calif., USA), a covalently modified version of the Taq DNA polymerase, reversibly inhibited by treatment with an acid anhydride (details can be found in U.S. Pat. Nos. 5,677,152 and 5,773,258).

2: Noncovalently modified enzyme:

Platinum® Taq DNA Polymerase (Invitrogen, Carlsbad, Calif., USA), a recombinant Taq DNA polymerase, which is complexed with an antibody that blocks the polymerase 5 activity at room temperature. By heating to 94° C., as typically occurs during the denaturation step, the antibody is denatured and the blocking is removed (details can be found in U.S. Pat. Nos. 5,338,671 and 5,587,287).

In order to investigate these with respect to the amplification of long DNA fragments, a 112 base pair fragment of the transcript for the human AK1 gene (NM_000476) was amplified. The primers used for this had the following sequences:

```
                                        (Seq ID No:5)
Forward primer: AAGAGAAGCTGAAGAAAACCAA (Seq ID No:6)
Reverse primer: GTGGAGAGGTGGGTGTAG
```

The amplification was carried out using the HotStarTaq PCR buffer, which contains Tris, potassium chloride, magnesium chloride and ammonium sulfate. Furthermore, SYBR Green at a final concentration of 0.1× and dNTP-nucleotides at a final concentration of 0.2 mM were added. The enzymes stated above were used as follows.

4. AmpliTaq Gold DNA polymerase alone: the amount used was 1.25 units per reaction (as recommended by the manufacturer)

5. Platinum Taq DNA polymerase alone: the amount used was 0.5 U (as recommended by the manufacturer)

6. A mixture of AmpliTaq Gold DNA polymerase (covalently modified enzyme) and Platinum Taq DNA polymerase (non-covalently modified enzyme), at a ratio of 0.125 units noncovalently modified enzyme to 1.25 units covalently modified enzyme per reaction.

The final volume of the reaction mixture was in each case 25 µl, and the primers were introduced at a final concentration of 0.7 µM. It was carried out on the Mx3005P Real-Time PCR System (Stratagene). 10 ng, 1 ng and 0.1 ng cDNA, prepared from HeLa-RNA, served as template per reaction. In each case 4 replicates were analyzed per enzyme or enzyme mixture and per amount of template.

The reaction conditions were as follows:

A: Initial denaturation of the template/activation of the enzyme

95° C., 10 minutes

B: Amplification:

Denaturation: 95° C., 15 seconds

Primer annealing: 55° C., 30 seconds

Primer extension: 72° C., 30 seconds

Fluorography during the extension in each cycle

Number of cycles: 45

C: Melting curve analysis

Initial denaturation of the PCR product: 95° C., 15 seconds

Rehybridization of the PCR product: 60° C., 20 seconds

Melting of the PCR product: heating from 60° C. to 95° C. at a heating rate of 0.1° C./s
Fluorography during melting of the PCR product The reaction mixtures were assayed at room temperature.

As can be seen from FIG. 3a, the desired 112 bp fragment was indeed successfully amplified using the noncovalently modified enzyme, as follows from the combined analysis of the amplification plot and the melting curve analysis. It is evident, however, that as well as the desired product with a melting temperature of approx. 88° C. there are still numerous other by-products, both with higher and with lower melting temperature. Reliable quantification is thus only possible to a limited degree.

FIG. 3b provides evidence of the failure of amplification of the same fragment when using only the covalently modified thermostable DNA polymerase. The increase in fluorescence occurs very late (starting from cycle 39 for the largest amount of template) for four replicates. Moreover, melting curve analysis shows that most of the products formed are undesirable, i.e. nonspecific amplificates. Their lower melting point compared with the specific product suggests that primer dimers are mainly formed here.

FIG. 3c provides evidence of the advantages of a combination of covalently and noncovalently modified enzymes, regardless of the type of modification. By adding a small amount of immediately-reactivated, noncovalently modified enzyme, as shown in FIGS. 3a and 3b there was a dramatic improvement in the results, greatly exceeding the results when using the two enzymes separately, both with respect to sensitivity (number of cycles when the threshold is crossed) and specificity (production of exclusively specific product).

Combining the results from Examples 1, 2 and 3, it can be concluded that a combination of covalently and noncovalently modified enzymes represents a universally usable enzyme system, which is able to meet the various requirements of PCR such as efficient amplification of long fragments or even specific amplification when using small amounts of template or unfavorable primer combinations.

The invention claimed is:

1. A composition comprising at least one first enzyme reversibly inhibited by chemical covalent modification as well as at least one second enzyme reversibly inhibited by noncovalent binding of a polyanion, wherein said second enzyme is a polymerase.

2. A kit comprising at least one first enzyme reversibly inhibited by chemical covalent modification and at least one second enzyme reversibly inhibited by noncovalent binding of a polyanion, wherein said second enzyme is a polymerase, or a mixture of the first and second enzymes.

3. A method for amplifying a nucleic acid, comprising:
amplifying a nucleic acid in the presence of the composition of claim 1.

4. The method of claim 3, wherein the amplifying takes place by PCR or coupled reverse transcription-PCR (one-step RT-PCR).

5. The composition of claim 1, wherein both the first and second enzymes are thermostable.

6. The composition of claim 1, wherein the inhibition of the first and second enzymes can be reversed by heat.

7. The composition of claim 1, wherein the first enzyme is a DNA polymerase, RNA polymerase, ligase, reverse transcriptase, restriction endonuclease or restriction exonuclease, and the second enzyme is a DNA or RNA polymerase.

8. The composition of claim 7, wherein both the first and second enzymes are thermostable DNA polymerases.

9. The composition of claim 1, wherein the unit ratio of the first enzyme to the second enzyme in the composition ranges from 0.1:1 to 100:1.

10. The composition of claim 1, further comprising additional components for a polymerase chain reaction (PCR) or coupled reverse transcription-PCR.

11. A method for processing a nucleic acid molecule, comprising processing a nucleic acid molecule in the presence of a first enzyme reversibly inhibited by chemical modification and a second enzyme reversibly inhibited by noncovalent binding.

12. The method of claim 11, wherein the processing of the nucleic acid molecule is performed by ligating the nucleic acid molecule with a second nucleic acid molecule.

13. The method of claim 11, wherein the processing of the nucleic acid molecule is performed by digesting the nucleic acid molecule.

14. The kit of claim 2, wherein the inhibition of the first and second enzymes can be reversed by heat.

15. The kit of claim 2, wherein the first enzyme is a DNA polymerase, RNA polymerase, ligase, reverse transcriptase, restriction endonuclease or restriction exonuclease, and the second enzyme is a DNA or RNA polymerase.

16. The kit of claim 2, wherein both the first and second enzymes are thermostable DNA polymerases.

17. The kit of claim 2, wherein the unit ratio of the first enzyme to the second enzyme in the mixture ranges from 0.1:1 to 100:1.

18. The method of claim 3, wherein the inhibition of the first and second enzymes can be reversed by heat.

19. The method of claim 3, wherein both the first and second enzymes are thermostable DNA polymerases.

20. The method of claim 3, wherein the unit ratio of the first enzyme to the second enzyme in the reaction mixture ranges from 0.1:1 to 100:1.

* * * * *